United States Patent
Coward et al.

(10) Patent No.: US 10,842,977 B2
(45) Date of Patent: *Nov. 24, 2020

(54) SYSTEM AND METHOD FOR REDUCED PRESSURE CHARGING

(71) Applicant: KCI Licensing, Inc., San Antonio, TX (US)

(72) Inventors: Christopher Guy Coward, Wareham (GB); Keith Patrick Heaton, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 433 days.

This patent is subject to a terminal disclaimer.

(21) Appl. No.: 15/792,265

(22) Filed: Oct. 24, 2017

(65) Prior Publication Data
US 2018/0043142 A1   Feb. 15, 2018

Related U.S. Application Data

(63) Continuation of application No. 13/728,712, filed on Dec. 27, 2012, now Pat. No. 9,827,403, which is a
(Continued)

(51) Int. Cl.
*A61H 7/00* (2006.01)
*A61M 1/00* (2006.01)
*A61M 27/00* (2006.01)

(52) U.S. Cl.
CPC .......... *A61M 27/00* (2013.01); *A61M 1/0023* (2013.01); *A61M 1/0066* (2013.01);
(Continued)

(58) Field of Classification Search
CPC .. A61M 27/00; A61M 1/0072; A61M 1/0088; A61M 1/0066; A61M 1/0023; A61M 2205/078
See application file for complete search history.

(56) References Cited

U.S. PATENT DOCUMENTS 1,355,846 A  10/1920  Rannells
2,547,758 A   4/1951  Keeling
(Continued)

FOREIGN PATENT DOCUMENTS

AU  550575 B2  3/1986
AU  745271 B2  3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Quang D Thanh (57) ABSTRACT

A reduced pressure treatment system includes a compressible chamber positionable beneath a foot of a user and being movable between an expanded position and a compressed position. The compressible chamber includes an inlet and an outlet. An inlet valve is in fluid communication with the inlet to prevent fluid within the compressible chamber from exiting the inlet, and an outlet valve is in fluid communication with the outlet to prevent fluid from entering the compressible chamber through the outlet. A biasing member is disposed within the compressible chamber to bias the compressible chamber toward the expanded position, and a manifold is positionable at a tissue site and in fluid communication with the inlet of the compressible chamber.

31 Claims, 5 Drawing Sheets

Related U.S. Application Data continuation of application No. 12/403,911, filed on Mar. 13, 2009, now Pat. No. 8,366,644.

(60) Provisional application No. 61/036,391, filed on Mar. 13, 2008.

(52) U.S. Cl.
CPC ........ *A61M 1/0072* (2014.02); *A61M 1/0088* (2013.01); *A61H 7/00* (2013.01); *A61M 2205/078* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Pleas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,617,650 A * | 4/1997 | Grim ............... A43B 7/147 36/154 |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,790,946 B2 * | 9/2010 | Mulligan ............ A61F 13/0203 602/57 |
| 8,366,644 B2 * | 2/2013 | Coward ............ A61M 1/0023 601/6 |
| 9,827,403 B2 * | 11/2017 | Coward ............ A61M 1/0023 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 1129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

(56) References Cited

FOREIGN PATENT DOCUMENTS

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/the British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", the Lancet, Sep. 3, 1983, pp. 532-534.
Chinn, Steven D. et al.: "Closed Wound Suction Drainage", the Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

SYSTEM AND METHOD FOR REDUCED PRESSURE CHARGING

CROSS-REFERENCE TO RELATED APPLICATIONS

This application is a continuation of U.S. Non-Provisional application Ser. No. 13/728,712 filed Dec. 27, 2012, which is a continuation of U.S. Non-Provisional application Ser. No. 12/403,911, filed Mar. 13, 2009, now U.S. Pat. No. 8,366,644 which claims the benefit of U.S. Provisional Application No. 61/036,391 filed Mar. 13, 2008, which is hereby incorporated by reference.

BACKGROUND OF THE INVENTION

1. Field of the Invention

The present application relates generally to tissue treatment systems and in particular to a system and method for reduced pressure charging.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment.

Reduced pressure treatment systems may include reduced pressure sources such as a powered pump that generates the reduced pressure that is delivered to a tissue site. However, such reduced pressure sources are often bulky or obtrusive to a user and are not readily adapted to be used in conjunction with foot treatment systems.

SUMMARY

The problems presented by existing reduced pressure treatment systems are solved by the systems and methods of the illustrative embodiments described herein. In one illustrative embodiment, a reduced pressure treatment system includes a compressible bladder positioned beneath a foot of a user. The compressible bladder includes a chamber substantially enclosed by a chamber wall, and the compressible bladder is movable between an expanded position and a compressed position to generate a reduced pressure. A resilient member is operatively associated with the chamber wall to bias the compressible bladder toward the expanded position. A manifold is positioned at a tissue site of the user and in fluid communication with the chamber of the compressible bladder.

In another illustrative embodiment, a reduced pressure treatment system is provided. The reduced pressure treatment system includes a compressible chamber positionable beneath a foot of a user and being movable between an expanded position and a compressed position. The compressible chamber includes an inlet and an outlet. An inlet valve is in fluid communication with the inlet to prevent fluid within the compressible chamber from exiting the inlet, and an outlet valve is in fluid communication with the outlet to prevent fluid from entering the compressible chamber through the outlet. A biasing member is disposed within the compressible chamber to bias the compressible chamber toward the expanded position, and a manifold is positionable at a tissue site and in fluid communication with the inlet of the compressible chamber.

In still another illustrative embodiment, a reduced pressure treatment system is provided and includes a compressible bladder positionable beneath a foot of a user. The compressible bladder includes a chamber and is movable between an expanded position and a compressed position. The system further includes a biasing member disposed within the chamber to bias the compressible bladder toward the expanded position. A pressure regulator having a first variable-volume cavity and a second variable-volume cavity is provided. The first variable-volume cavity is fluidly connected to the chamber of the compressible bladder, and a manifold is positionable at a tissue site and in fluid communication with the second variable-volume cavity of the pressure regulator.

In yet another illustrative embodiment, a method for providing a reduced pressure to a reduced pressure tissue treatment system used by a user is provided. The method includes compressing a compressible bladder with a foot of the user and generating the reduced pressure within a chamber of the compressible bladder as the compressible bladder expands.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
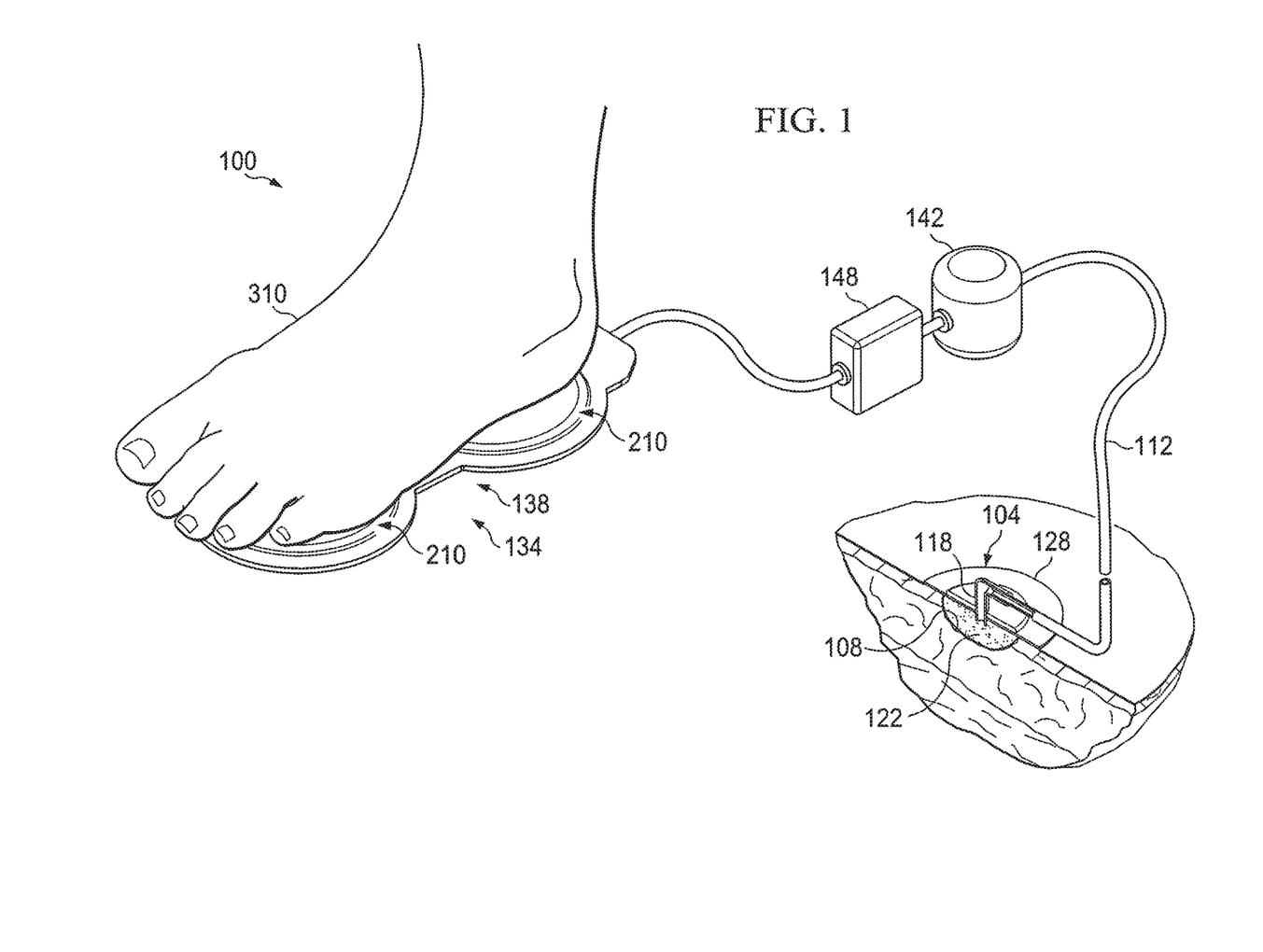
FIG. 1 illustrates a schematic of a reduced pressure treatment system having a compressible bladder system according to an illustrative embodiment.

Referring to FIG. 1, a reduced pressure treatment system 100 according to an illustrative embodiment includes a reduced pressure dressing 104 positioned at a tissue site 108 of a patient. The reduced pressure dressing 104 may include a distribution manifold 122 that is positioned adjacent to or in contact with the tissue site 108 to distribute a reduced pressure supplied by a reduced pressure source 134. The distribution manifold 122 may be any material, either bioabsorbable or non-bioabsorbable, that is capable of manifolding a reduced pressure to the tissue site 108. In one embodiment, the distribution manifold 122 is a porous foam and includes a plurality of interconnected cells or pores that act as flow channels. The porous foam may be a polyurethane, open-cell, reticulated foam such as GranuFoam® dressing manufactured by Kinetic Concepts, Inc. of San Antonio, Tex. If an open-cell foam is used, the porosity and pore size may vary, but in one embodiment, the pore size associated with the open-cell foam is about 400 to 600 microns. The flow channels allow fluid communication throughout the portion of the distribution manifold 122 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through distribution manifold 122.

Distribution manifold 122 may also be constructed from bioresorbable materials that do not need to be removed from a patient's body following use of reduced pressure treatment system 100. Suitable bioresorbable materials may include, without limitation, a polymeric blend of polylactic acid (PLA) and polyglycolic acid (PGA). The polymeric blend may also include without limitation polycarbonates, polyfumarates, polyhydroxybutarates, polyhydroxyvalerates, polysaccharides, polyaminoacids, and capralactones. Distribution manifold 122 may further serve as a scaffold for new cell-growth, or a scaffold material may be used in conjunction with distribution manifold 122 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-fraction (i.e., a high content of air).

The distribution manifold 122 is fluidly connected to the reduced pressure source 134 by a conduit 112. The conduit 112 may fluidly communicate with the distribution manifold 122 through a tubing adapter 118 positioned adjacent to the distribution manifold 122. A drape 128 may be placed over the distribution manifold 122 and sealed around a perimeter of the tissue site 108 to maintain reduced pressure at the tissue site 108.

In the embodiment illustrated in FIG. 1, the reduced pressure source 134 is a compressible bladder system 138 that is manually-actuated by a user to provide the reduced pressure to the tissue site. The compressible bladder system 138 is described in more detail below with reference to FIGS. 2 and 3. Delivery of reduced pressure to the reduced pressure dressing 104 and tissue site 108 encourages new tissue growth by maintaining drainage of exudate from the tissue site 108, increasing blood flow to tissues surrounding the tissue site 108, and creating microstrain at the tissue site 108.

Referring still to FIG. 1, a canister 142 may be fluidly connected between the reduced pressure source 134 and the tissue site 108 to collect exudate and other fluids drawn from the tissue site 108. The canister 142 includes an inlet that is fluidly connected to the conduit 112 and an outlet that is fluidly connected to the reduced pressure source 134. A liquid-air separator (not shown), such as for example a hydrophobic filter, may be operatively associated with the outlet of the canister 142 to prevent liquid from exiting the canister 142 through the outlet. The liquid-air separator prevents the reduced pressure source 134 from becoming contaminated by exudate and other biologically contaminative materials. As an alternative to the canister 142, or in addition to the canister 142, the reduced pressure treatment system 100 may include additional dressing components at the tissue site 108 that are capable of storing exudate and other liquids at or near the tissue site. For example, the reduced pressure dressing 104 positioned at the tissue site 108 may include, in addition to the distribution manifold 122, one or more absorbent layers that permit storage of liquid within the reduced pressure dressing 104. The liquid storage capabilities of such a dressing may be used in lieu of or in addition to the canister 142.

A pressure regulator 148 may be fluidly connected between the compressible bladder system 138 and the canister 142 to regulate and control the amount of pressure delivered to the canister 142 and the tissue site 108. The pressure regulator may be any device that is capable of regulating or controlling a reduced pressure or a positive pressure. In one embodiment, the pressure regulator 148 is provided to ensure that the reduced pressure delivered to the tissue site 108 does not exceed a threshold amount. In other words, the pressure regulator ensures that the absolute pressure supplied to the tissue site 108 is not too low. A vent (not shown) may be associated with the pressure regulator 148 to raise the absolute pressure within the pressure regulator if more reduced pressure than is needed is provided by the compressible bladder system 138. The vent may operate by allowing ambient air into the pressure regulator when the absolute pressure within the pressure regulator 148 drops below a predetermined value.

In addition to the canister 142 and pressure regulator 148, the reduced pressure treatment system 100 may also include sensors, processing units, alarm indicators, memory, databases, software, display units, and user interfaces that further facilitate the application of reduced pressure treatment to the tissue site 108. In one example, a sensor (not shown) may be disposed at or near the reduced pressure source 134 to determine a source pressure generated by the reduced pressure source 134. The sensor may communicate with a processing unit that monitors and controls the reduced pressure that is delivered by the reduced pressure source 134.

Figure 2:
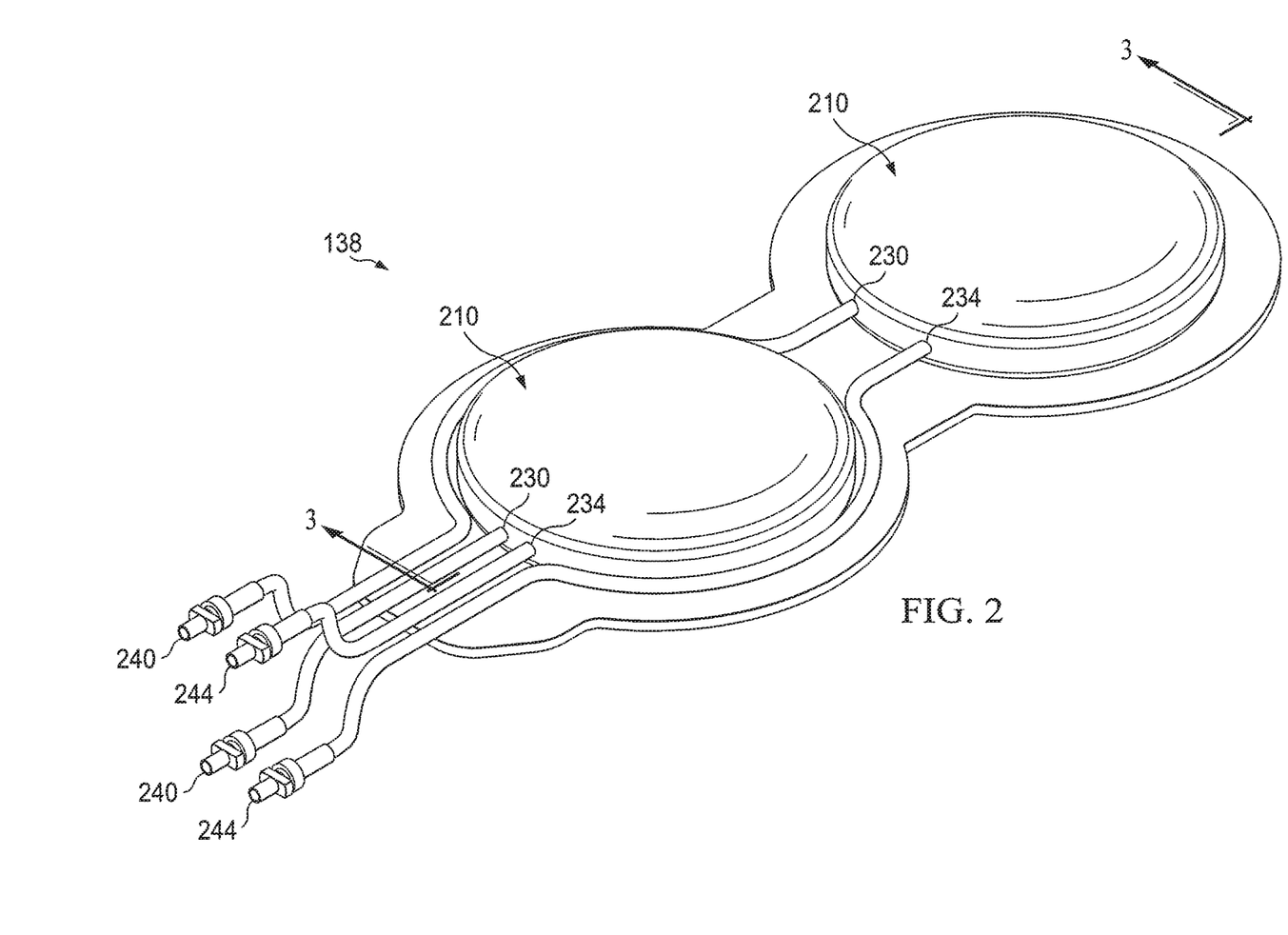
FIG. 2 depicts a perspective view of the compressible bladder system of FIG. 1.
Figure 3A:
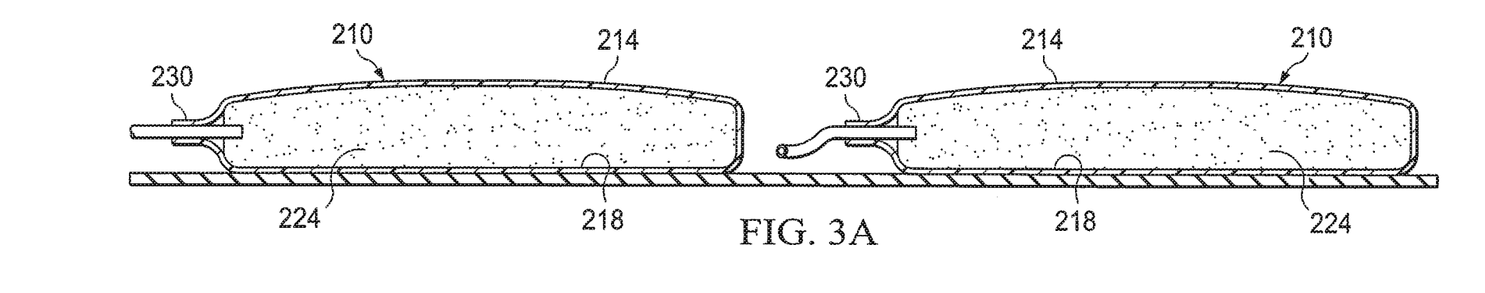
FIG. 3A illustrates a cross-sectional side view of the compressible bladder system of FIG. 2 taken at 3-3, the bladder system being shown in an expanded position.
Figure 3B:
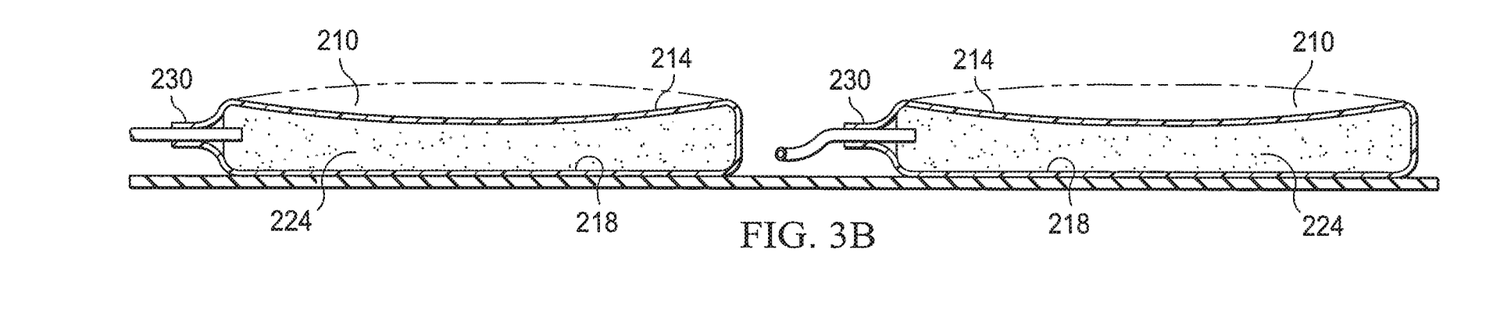
FIG. 3B depicts a cross-sectional side view of the compressible bladder system of FIG. 2 taken at 3-3, the bladder system being shown in a compressed position.

Referring to FIGS. 2, 3A, and 3B, the compressible bladder system 138 includes a pair of compressible bladders 210. Each compressible bladder 210 includes a chamber wall 214 that substantially encloses a chamber 218. The compressible bladder 210 is movable between an expanded position (see FIG. 3A) and a compressed position (see FIG. 3B). A biasing member 224, or resilient member, is disposed within the chamber 218 to bias the compressible bladder 210 toward the expanded position. In one embodiment, the biasing member 224 is an open-cell foam such as, for example, a reticulated polyurethane foam similar to that used with the distribution manifold 122. In another embodiment, the biasing member may be a spring, sponge, or any other type of resilient material or structure that is capable of returning the compressible bladder 210 to the expanded position following compression of the compressible bladder 210. In still another embodiment, the biasing member 224 may be positioned external of the chamber 218 and still have a biasing effect that urges the compressible bladder 210 toward the expanded position. For example, the biasing member 224 may include a resilient material that is bonded, welded, or other attached to or integrated into the chamber wall 214 that causes the chamber wall 214 to resiliently return to the expanded position. In one embodiment, the biasing member 224 may include the chamber wall 214 without additional structures, components, or materials. More specifically, if the chamber wall 214 is made from a sufficiently resilient material, the chamber wall 214 may attempt to return the compressible bladder 210 to the expanded position after the compressive force has been removed.

The chamber 218 of each compressible bladder 210 includes an inlet 230 and an outlet 234. An inlet valve 240 is in fluid communication with the inlet 230 to prevent fluid exiting the chamber 218 from passing through the inlet 230. An outlet valve 244 is in fluid communication with the outlet 234 to prevent fluid from entering the chamber 218 through the outlet 234. The inlet valve 240 and outlet valve 244 may be positioned in conduits fluidly connected to the inlet 230 and outlet 234, respectively, as shown in FIG. 2. Alternatively, the inlet valve 240 and outlet valve 244 may be more directly associated with or positioned within inlet and outlet ports on the compressible bladder 210. The inlet valve 240 and outlet valve 244 may be any particular type of valve for selectively inhibiting or preventing fluid flow, but in one embodiment, the valves 240, 244 are one-way valves such as check valves to allow fluid flow in one direction and prevent fluid flow in another direction. One example of a check valve that may be used with the compressible bladders 210 is a flapper-type valve that includes a flapper positioned over an aperture in the chamber wall 214. As fluid pressure on one side of the aperture builds, the flapper moves to an open position to allow fluid communication through the aperture. As fluid pressure on the other side of the aperture increases, the flapper is moved against the aperture to block fluid communication.

Referring still to FIGS. 2, 3A, and 3B, but also to FIG. 1, in operation the compressible bladders 210 are positioned beneath a foot 310 of a user. One of the compressible bladders 210 is preferably positioned under a heel region 314 of the foot 310, and another of the compressible bladders 210 is preferably positioned under a forefoot region 318 of the foot 310. As the weight of the user is exerted on a particular compressible bladder 210, the compressible bladder 210 is compressed to the compressed position (see FIG. 3B) and gas (e.g. air) that is within the chamber 218 is ejected through the outlet 234 and the outlet valve 244. The gas that is ejected from the chamber 218 is prevented from exiting the inlet 230 due to the presence of the inlet valve 240. As the weight of the user is lifted from the compressible bladder 210 that has been compressed, the compressible bladder 210 begins to move toward the expanded position. The movement of the compressible bladder 210 toward the expanded position is aided by the biasing member 224. As the compressible bladder 210 expands, a volume of the chamber 218 increases, which creates a reduced pressure within the chamber 218 relative to ambient pressure surrounding the compressible bladder 210. This reduced pressure within the chamber 218 pulls fluid into the chamber 218 through the inlet valve 240 and the inlet 230. Fluid is prevented from entering the chamber 218 through the outlet 234 due to the presence of the outlet valve 244. The reduced pressure generated by the compressible bladder 210 during expansion may be transmitted to the distribution manifold 122 by fluidly connecting the manifold 122 to the inlet 230 of the compressible bladder 210.

The positioning of the compressible bladders 210 under the heel region 314 and forefoot region 318 of the foot 310 allows a more consistent application of reduced pressure as the user cyclically applies weight to the heel region 314 and then to the forefoot region 318. Such a regimen of weight distribution is consistent with normal walking or running activities, and the compressible bladder system 138 is particularly suited for generating reduced pressure while a user is walking or running. As the user distributes weight to the heel region 314, the compressible bladder 210 under the heel region 314 compresses to the compressed position. As the user's weight shifts to the forefoot region 318, the compressible bladder 210 under the forefoot region 318 compresses to the compressed position. The shifting of weight to the forefoot region 318 relieves the compressive force on the compressible bladder 210 near the heel region 314, thereby allowing the compressible bladder 210 under the heel region to expand and generate reduced pressure. When the user's weight shifts back to the heel region 314, the compressible bladder 210 under the forefoot region 318 expands, thereby generating reduced pressure. This cycle continues as the user continues walking, which permits a generation of reduced pressure.

Figure 4:
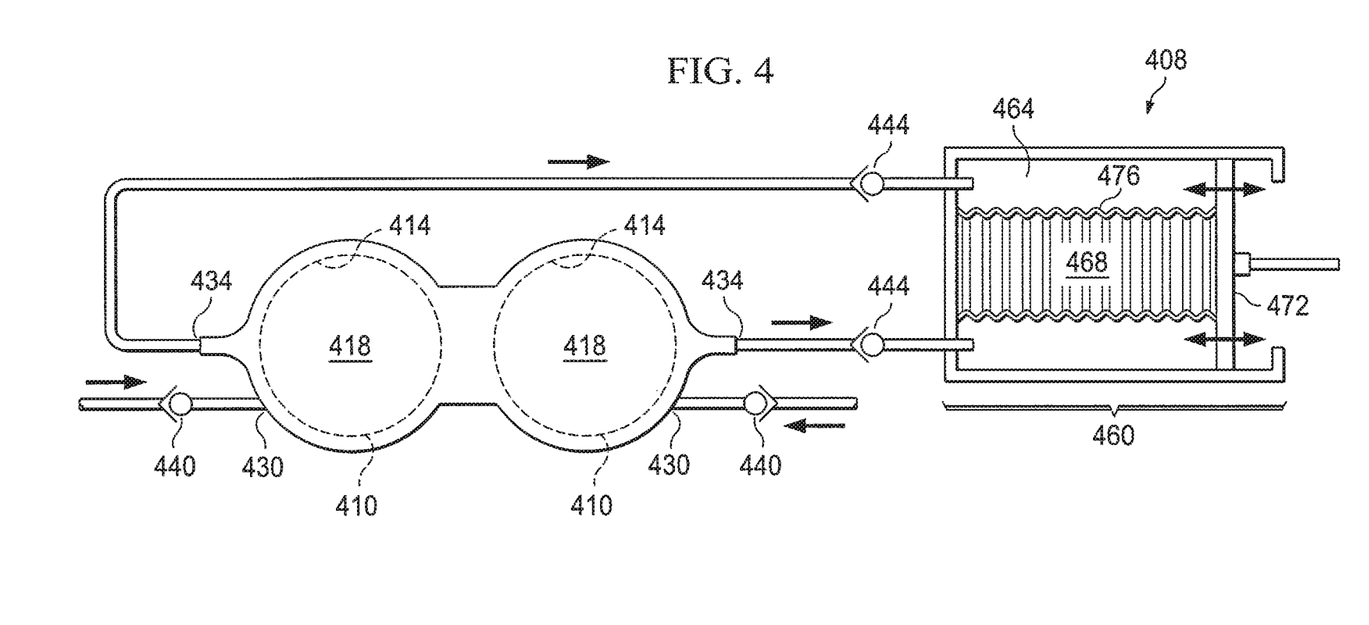
FIG. 4 illustrates a schematic of a compressible bladder system and pressure regulator according to an illustrative embodiment.

Referring to FIG. 4, a compressible bladder system 408 similar to compressible bladder system 138 is illustrated. The compressible bladder system 138 includes a pair of compressible bladders 410. Each compressible bladder 410 includes a chamber wall 414 that substantially encloses a chamber 418. The compressible bladder 410 is movable between an expanded position and a compressed position similar to those previously described with reference to FIGS. 3A and 3B. A biasing member, or resilient member, (not shown) is disposed within the chamber 418 to bias the compressible bladder 410 toward the expanded position. The biasing member is similar in structure and function to the biasing member 224 previously described.

The chamber 418 of each compressible bladder 410 includes an inlet 430 and an outlet 434. An inlet valve 440 is in fluid communication with the inlet 430 to prevent fluid exiting the chamber 418 from passing through the inlet 430. An outlet valve 444 is in fluid communication with the outlet 434 to prevent fluid from entering the chamber 418 through the outlet 434. The inlet valve 440 and outlet valve 444 may be positioned in conduits fluidly connected to the inlet 430 and outlet 434, respectively, as shown in FIG. 4. Alternatively, the inlet valve 440 and outlet valve 444 may be more directly associated with or positioned within inlet and outlet ports on the compressible bladder 410. The inlet valve 440 and outlet valve 444 are similar in structure and function to the valves previously described herein.

In the embodiment illustrated in FIG. 4, the compressible bladder system 408 includes a pressure regulator 460 having a first variable-volume cavity 464 and a second variable-volume cavity 468. In one embodiment, the cavities 460, 468 share a common piston wall 472 that is movable between a retracted position (not shown) and an extended position (see FIG. 4) to vary the volume associated with the cavities 460, 468. The cavities 460, 468 are fluidly separated from each other by a divider 476. In one illustrative embodiment, the divider 476 may be a bellows that is formed from a sufficiently resilient material.

Each of the cavities 464, 468 includes an outlet (not shown) and a one-way valve (not shown) so that air or other gases within the cavities 464, 468 may be expelled from the cavities 464, 468 when the piston wall 472 is moved to a retracted position. A user may place the piston wall 472 in the retracted position by exerting a compressive force on the piston wall.

The outlet 434 of each compressible bladder 410 is fluidly connected to the first variable-volume cavity 464. When the piston wall 472 has been positioned in the retracted position, the positively pressured gas from the outlet 434 may bias the piston wall 472 toward the extended position (see FIG. 4). As the piston wall 472 moves toward the extended position, the volume of the second variable-volume cavity 468 increases, which generates a reduced pressure within the second variable-volume cavity 468. The reduced pressure generated by the compressible bladders 410 and pressure regulator 460 during expansion of the second variable-volume cavity 468 may be transmitted to the distribution manifold 122 by fluidly connecting the manifold 122 to the second variable-volume cavity 468 of the pressure regulator 460.

Figure 5:
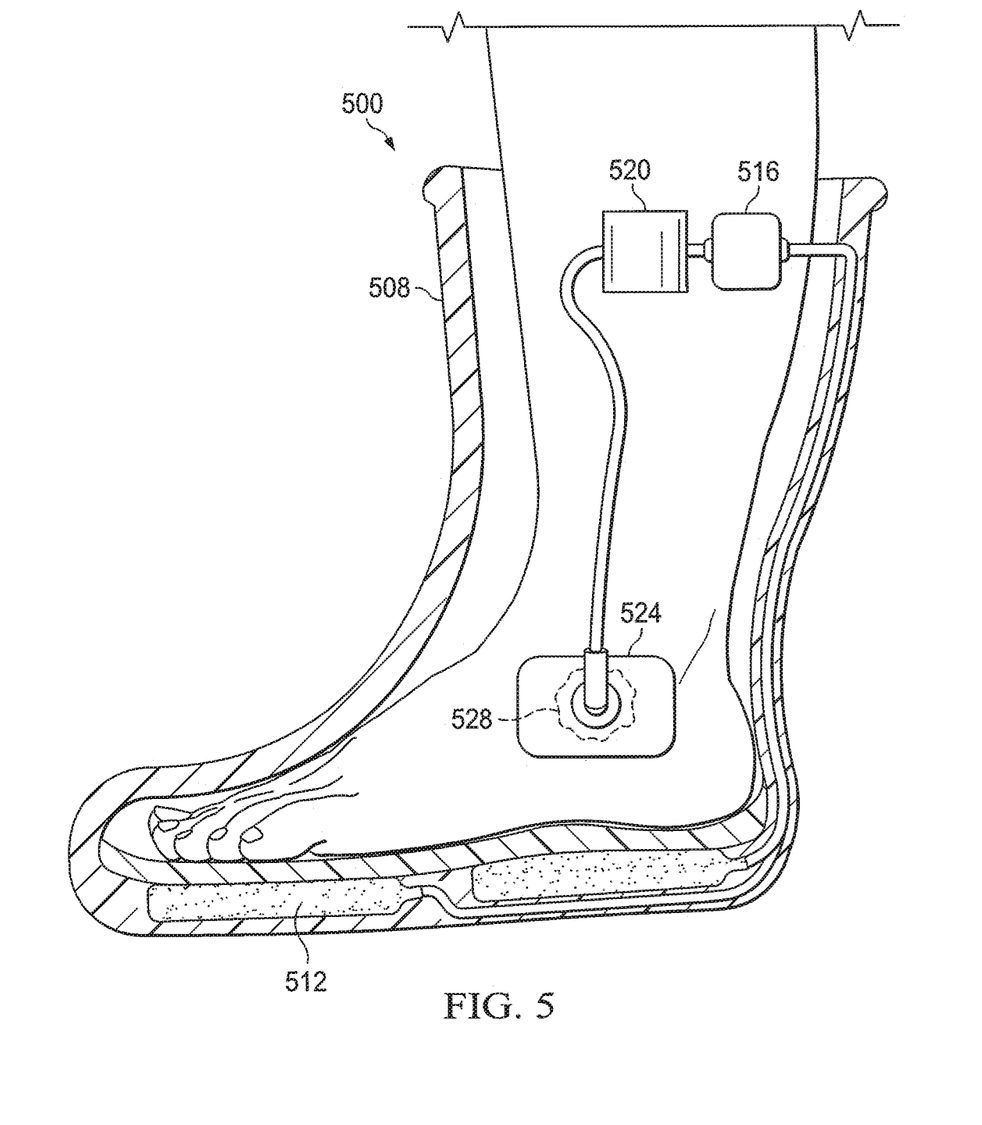
FIG. 5 depicts an article of orthotic footwear having a compressible bladder system according to an illustrative embodiment.

Referring to FIG. 5, a reduced pressure treatment system 500 according to an illustrative embodiment includes an article of footwear 508 having a compressible bladder system 512 which may be similar to any of the compressible bladder systems described herein. In one embodiment, the compressible bladder system 512 is fluidly connected to a pressure regulator 516 and a canister 520. The canister 520 may be fluidly connected to a reduced pressure dressing 524 positioned at a tissue site 528. The reduced pressure generated by the compressible bladder system 512 and/or the pressure regulator 516 is delivered to the tissue site 528 through the reduced pressure dressing 524, which preferably includes a distribution manifold (not shown). While the tissue site 528 has been illustrated on a side of a foot stabilized within the article of footwear 508, the tissue site 528 may instead be located in the plantar region of the foot or on any other region of the foot or lower extremities. Alternatively, the tissue site 528 may be located on other parts of the body.

The article of footwear 508 may be an offloading boot, cast walker, neuropathic walker, or any other type of orthotic or therapeutic footwear. The article of footwear 508 is particularly well suited, when equipped with the compressible bladder system 512 to treat diabetic foot ulcers and other foot-related injuries and wounds. The article of footwear 508 may be designed to relieve pressure in injured areas of the foot of a patient, thereby allowing the patient to remain ambulatory. As the patient walks, the compressible bladder system 512 is activated as previously described to generate reduced pressure. This reduced pressure may be directed to the injuries or wounds of the patient to improve healing through reduced pressure treatment.

A method for providing a reduced pressure to a reduced pressure tissue treatment system used by a user is provided. The method includes compressing a compressible bladder with a foot of the user, and generating the reduced pressure within a chamber of the compressible bladder as the compressible bladder expands. The compressible bladder may be similar to any of the compressible bladders or compressible bladder systems described herein. In one embodiment, the method may further include compressing a second compressible bladder with the foot of the user and generating a second reduced pressure within a second chamber of the second compressible bladder as the second compressible bladder expands. The second reduced pressure may be substantially the same as the first reduced pressure, or alternatively may be a higher or lower pressure. When two compressible bladders are provided, the first compressible bladder is positioned under a forefoot region of the foot and is compressed when the user places weight on the forefoot region. The second compressible bladder is positioned under a heel region of the foot and is compressed when the user places weight on the heel region. In this manner, both of the compressible bladders are compressed and expanded during a single stride of the user while walking.

While the compressible bladders described herein are positionable beneath a foot of a user, the compressible bladders may instead be compressed by applying a force from another part of the body or some other object. Additionally, while a compressible bladder system having two compressible bladders is illustrated, a single compressible bladder may be used, or alternatively, multiple compressible bladders in excess of two may be used. In one illustrative embodiment, when multiple compressible bladders are used, each of the compressible bladders is fluidly independent, and each compressible bladder includes one-way valves or devices associated with the inlet and outlet of the compressible bladder.

The pressure regulators described herein may serve to regulate or control the pressure supplied by the compressible bladder system. With respect to pressure regulator 460, the pressure regulator may further be used to provide a reduced pressure to a tissue site when a positive pressure is supplied to the pressure regulator. While the use of pressure regulators may be preferred in some embodiments, in other embodiments, a pressure regulator may be omitted. In these embodiments that do not include a separate pressure regulator, the compressible bladder may be configured to be self-regulating based on the sizing, shape, and material used for the compressible bladder and the biasing member. For example, in one embodiment, as the reduced pressure at the tissue site and in the conduit leading to the tissue site increases, the compressible bladder continues to supply additional reduced pressure as long as the resiliency of the biasing member or the chamber wall of the compressible bladder is able to overcome the tendency of the compressible bladder to remain collapsed. When the biasing member or chamber wall is no longer able to expand following compression due to the amount of reduced pressure in the conduit leading to the tissue site, the compressible bladder will no longer generate additional reduced pressure.

It should be apparent from the foregoing that an invention having significant advantages has been provided. While the invention is shown in only a few of its forms, it is not just limited but is susceptible to various changes and modifications without departing from the spirit thereof.

We claim:

1. A reduced-pressure source for operation by a foot to supply a reduced pressure to a tissue site, the reduced-pressure source comprising:
   a compressible bladder adapted to be positioned beneath the foot, the compressible bladder having a chamber substantially enclosed by a chamber wall and being movable between an expanded position and a compressed position, wherein transitioning from the compressed position to the expanded position causes the reduced pressure to be delivered to the tissue site;
   a biasing member positioned within the chamber to bias the compressible bladder toward the expanded position;
   an inlet valve in fluid communication with an inlet of the compressible bladder to prevent fluid within the chamber from exiting the inlet;
   an outlet valve in fluid communication with an outlet of the compressible bladder to prevent fluid from entering the chamber through the outlet; and
   a pressure regulator fluidly connected to the chamber and adapted to regulate the reduced pressure delivered to the tissue site.

2. The reduced-pressure source of claim 1, wherein the pressure regulator comprises a vent configured to raise an absolute pressure within the pressure regulator when the reduced pressure provided by the compressible bladder exceeds a threshold amount.

3. The reduced-pressure source of claim 1, wherein the pressure regulator comprises a vent configured to allow ambient air into the pressure regulator when the absolute pressure within the pressure regulator drops below a predetermined value.

4. The reduced-pressure source of claim 1, wherein the pressure regulator comprises a vent configured to regulate the reduced-pressure that is delivered to the tissue site by allowing ambient air into the pressure regulator.

5. The reduced-pressure source of claim 1, wherein the compressible bladder is adapted to generate a reduced pressure within the chamber as the compressible bladder moves toward the expanded position.

6. The reduced-pressure source of claim 1, wherein the biasing member is an open-cell foam.

7. The reduced-pressure source of claim 1, wherein the biasing member is bonded to the chamber wall.

8. The reduced-pressure source of claim 1, wherein the biasing member is welded to the chamber wall.

9. The reduced-pressure source of claim 1, wherein the compressible bladder is a first compressible bladder, the reduced-pressure source further comprising:
   a second compressible bladder adapted to be positioned beneath the foot, the second compressible bladder having a second chamber substantially enclosed by a second chamber wall and being movable between an expanded position and a compressed position; and
   a second biasing member positioned within the second chamber to bias the second compressible bladder toward the expanded position.

10. The reduced-pressure source of claim 9, wherein the first compressible bladder is adapted to be positioned beneath a forefoot region of the foot and the second compressible bladder is adapted to be positioned beneath a heel region of the foot.

11. The reduced-pressure source of claim 1, wherein the compressible bladder is a first compressible bladder, the reduced-pressure source further comprising:
   a second compressible bladder adapted to be positioned beneath the foot, the second compressible bladder having an inlet, an outlet, and a second chamber substantially enclosed by a second chamber wall, and being movable between an expanded position and a compressed position;
   a second biasing member positioned within the second chamber to bias the second compressible bladder toward the expanded position;
   an inlet valve in fluid communication with the inlet of the second compressible bladder to prevent fluid within the second chamber from exiting the inlet; and
   an outlet valve in fluid communication with the outlet of the second compressible bladder to prevent fluid from entering the second chamber through the outlet.

12. The reduced-pressure source of claim 1, wherein:
   the pressure regulator comprises a first variable-volume cavity fluidly connected to the chamber of the compressible bladder; and
   the first variable-volume cavity is configured to expand as the first variable-volume cavity receives a positively pressured air from the chamber.

13. The reduced-pressure source of claim 12, wherein:
   the pressure regulator comprises a second variable-volume cavity; and
   the second variable-volume cavity is configured to expand and generate a reduced pressure as the first variable-volume cavity expands.

14. The reduced-pressure source of claim 12, wherein:
   the pressure regulator comprises a second variable-volume cavity; and
   the pressure regulator includes a bellows device fluidly separating the first variable-volume cavity and the second variable-volume cavity.

15. A reduced-pressure source for operation by a foot to supply a reduced pressure to a tissue site, the reduced-pressure source comprising:
   a first compressible bladder adapted to be positioned beneath a forefoot region of the foot, the first compressible bladder having a first chamber substantially enclosed by a first chamber wall and being movable between an expanded position and a compressed position, wherein the first compressible bladder comprises a first inlet and a first outlet;

a first biasing member positioned within the first chamber to bias the first compressible bladder toward the expanded position;
a first inlet valve in fluid communication with the first inlet to prevent fluid within the first compressible bladder from exiting the first inlet;
a first outlet valve in fluid communication with the first outlet to prevent fluid from entering the first compressible bladder through the first outlet;
a second compressible bladder adapted to be positioned beneath a heel region of the foot, the second compressible bladder having a second chamber substantially enclosed by a second chamber wall and being movable between an expanded position and a compressed position; and
a second biasing member positioned within the second chamber to bias the second compressible bladder toward the expanded position.

16. The reduced-pressure source of claim 15, further comprising:
a second inlet valve in fluid communication with a second inlet of the second compressible bladder to prevent fluid within the second chamber from exiting the second inlet of the second compressible bladder; and
a second outlet valve in fluid communication with a second outlet of the second compressible bladder to prevent fluid from entering the second chamber through the second outlet of the second compressible bladder.

17. The reduced-pressure source of claim 15, wherein the first compressible bladder is adapted to generate a reduced pressure within the first chamber as the first compressible bladder moves toward the expanded position.

18. The reduced-pressures source of claim 15, wherein the first biasing member is an open-cell foam.

19. The reduced-pressure source of claim 15, further comprising a pressure regulator fluidly connected to the first chamber and adapted to regulate the reduced pressure delivered to the tissue site.

20. The reduced-pressure source of claim 19, wherein:
the pressure regulator comprise a variable-volume cavity fluidly connected to the first chamber; and
the variable-volume cavity is configured to expand as the variable-volume cavity receives a positively pressured air from the first chamber.

21. The reduced-pressure source of claim 19, wherein:
the pressure regulator has a first variable-volume cavity and a second variable-volume cavity, the first variable-volume cavity being fluidly connected to the first chamber; and
the second variable-volume cavity is configured to expand and generate a reduced pressure as the first variable-volume cavity expands.

22. The reduced-pressure source of claim 19, wherein:
the pressure regulator has a first variable-volume cavity and a second variable-volume cavity, the first variable-volume cavity being fluidly connected to the first chamber;
the first variable-volume cavity is configured to expand as the first variable-volume cavity receives a positively pressured air from the first chamber; and
the second variable-volume cavity is configured to expand and generate a reduced pressure as the first variable-volume cavity expands.

23. The reduced-pressure source of claim 19, wherein:
the pressure regulator has a first variable-volume cavity and a second variable-volume cavity, the first variable-volume cavity being fluidly connected to the first chamber of the first compressible bladder; and
the pressure regulator includes a bellows device fluidly separating the first variable-volume cavity from the second variable-volume cavity.

24. A system for regulating reduced pressure provided to a tissue site, the system comprising:
a reduced pressure source comprising a compressible bladder having a chamber; and
a pressure regulator configured to be fluidly connected to the reduced-pressure source, the pressure regulator comprising:
a first variable-volume cavity of the pressure regulator that is fluidly connected to the chamber of the compressible bladder, and
a second variable-volume cavity configured to be fluidly coupled to the tissue site,
wherein the first variable-volume cavity is configured to expand and generate a reduced pressure within the second variable-volume cavity as the first variable-volume cavity expands, and
wherein the second variable-volume cavity is configured to expand and generate a reduced pressure at the tissue site as the first variable-volume cavity expands.

25. The system of claim 24, wherein:
the chamber is substantially enclosed by a chamber wall, the chamber being movable between an expanded position and a compressed position; and
a biasing member configured to bias the compressible bladder toward the expanded position.

26. The system of claim 25, wherein the compressible bladder is configured to generate a reduced pressure within the chamber as the compressible bladder moves toward the expanded position.

27. The system of claim 25, wherein the compressible bladder is a first compressible bladder, the system further comprising:
a second compressible bladder adapted to be positioned beneath a foot, the second compressible bladder having a second chamber substantially enclosed by a second chamber wall and being movable between an expanded position and a compressed position; and
a second biasing member positioned within the second chamber to bias the second compressible bladder toward the expanded position.

28. The system of claim 27, wherein the first compressible bladder is adapted to be positioned beneath a forefoot region of the foot and the second compressible bladder is adapted to be positioned beneath a heel region of the foot.

29. The system of claim 25, further comprising:
an inlet valve in fluid communication with an inlet of the compressible bladder to prevent fluid within the chamber from exiting the inlet; and
an outlet valve in fluid communication with an outlet of the compressible bladder to prevent fluid from entering the chamber through the outlet.

30. The system of claim 27, wherein:
the first variable-volume cavity is configured to expand as the first variable-volume cavity receives a positively pressured air from the chamber.

31. The system of claim 27, wherein the pressure regulator includes a bellows device fluidly separating the first variable-volume cavity and the second variable-volume cavity.

* * * * *

UNITED STATES PATENT AND TRADEMARK OFFICE
CERTIFICATE OF CORRECTION

PATENT NO. : 10,842,977 B2  
APPLICATION NO. : 15/792265  
DATED : November 24, 2020  
INVENTOR(S) : Keith Patrick Heaton Page 1 of 1

It is certified that error appears in the above-identified patent and that said Letters Patent is hereby corrected as shown below:

On the Title Page

<u>On Page 3, Column 1, Under (Other Publications)</u>  
Line 7, delete "Philidelphia," and insert -- Philadelphia, --, therefor.

<u>On Page 3, Column 2, Under (Other Publications)</u>  
Line 43, delete "Hypermia" and insert -- Hyperemia --, therefor.

In the Specification

<u>Column 4</u>  
Line 8, delete "polyhydroxybutarates," and insert  
-- polyhydroxybutyrates, --, therefor.  
Line 9, delete "capralactones." and insert -- caprolactones. --, therefor.  
Line 18, delete "hydroxy apatites," and insert -- hydroxyapatites, --, therefor.

In the Claims

<u>Column 11</u>  
Line 33, in Claim 18, delete "reduced-pressures" and insert  
-- reduced-pressure --, therefor.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*